(12) United States Patent
Adams et al.

(10) Patent No.: US 6,582,685 B1
(45) Date of Patent: Jun. 24, 2003

(54) HYDROXYL-FUNCTIONALIZED DENDRITIC MACROMOLECULES IN TOPICAL COSMETIC AND PERSONAL CARE COMPOSITIONS

(75) Inventors: Gerald Adams, Wirral (GB); Melanie Ruth Ashton, Wirral (GB); Ezat Khoshdel, Wirral (GB)

(73) Assignee: Unilever Home & Personal Care USA, division of Conopco, Inc., Chicago, IL (US)

( * ) Notice: Subject to any disclaimer, the term of this patent is extended or adjusted under 35 U.S.C. 154(b) by 0 days.

(21) Appl. No.: 09/650,057

(22) Filed: Aug. 29, 2000

(30) Foreign Application Priority Data

Sep. 2, 1999 (GB) ............................................. 9920770

(51) Int. Cl.$^7$ .......................... A61K 7/075; A61K 9/10; A61K 47/34
(52) U.S. Cl. ...................... 424/70.11; 424/45; 424/486; 424/DIG. 1; 424/401; 516/104; 510/126
(58) Field of Search ................................ 424/45, 70.11, 424/486, DIG. 1, DIG. 2, DIG. 16, 401; 525/437, 242; 510/119, 126; 516/104

(56) References Cited

U.S. PATENT DOCUMENTS

| 5,418,301 | A | * | 5/1995 | Hult et al. .................. 525/437 |
| 5,449,519 | A | | 9/1995 | Wolf et al. |
| 5,663,247 | A | * | 9/1997 | Sorenson et al. ............ 525/533 |
| 6,068,835 | A | * | 5/2000 | Franzke et al. ........... 424/70.11 |
| 6,114,458 | A | * | 9/2000 | Hawker et al. .............. 525/242 |
| 6,287,552 | B1 | * | 9/2001 | Tournilhac et al. ....... 424/78.03 |
| 6,379,683 | B1 | * | 4/2002 | Simonnet et al. ........... 424/401 |

FOREIGN PATENT DOCUMENTS

| EP | 0987016 | 3/2000 |
| EP | 0987017 | 3/2000 |

OTHER PUBLICATIONS

International Search Report Application No. PCT/EP 00/08077 mailed Dec. 28, 2000.

Search Report under Section 17 Application No. GB 9920770.6 dated Dec. 14, 1999.

* cited by examiner

*Primary Examiner*—Edward J. Webman
(74) *Attorney, Agent, or Firm*—Milton L. Honig

(57) ABSTRACT

The invention provides a cosmetic and personal care composition, preferably a hair styling composition such as spray, gel or mousse, comprising a hydroxyl-functionalized dendritic macromolecule. Preferably the dendritic macromolecule is built up from polyester units.

9 Claims, No Drawings

HYDROXYL-FUNCTIONALIZED DENDRITIC MACROMOLECULES IN TOPICAL COSMETIC AND PERSONAL CARE COMPOSITIONS

FIELD OF THE INVENTION

The present invention relates to cosmetic and personal care compositions, such as hair styling compositions, containing hydroxyl-functionalised dendritic macromolecules.

BACKGROUND AND PRIOR ART

Cosmetic and personal care compositions such as hair styling sprays, mousses, gels and shampoos, frequently contain resins, gums and adhesive polymers to provide a variety of benefits, for example, film-forming ability, thickening, sensory properties and hair shaping and setting.

Such materials must meet a number of functional requirements. These include for example good hair holding ability and curl retention without giving a harsh, brittle feeling to the hair. Even under humid conditions there must be good hold and curl retention. Another requirement is that the material be capable of being removed upon washing the hair at the time of shampooing. Further important material properties are low stickiness and a lack of powdering or flaking.

We have found that hydroxyl-functionalised dendritic macromolecules are a class of material that meets the above requirements in a cosmetic and personal care composition, particularly hair styling compositions such as hairsprays.

Dendritic macromolecules are macromolecules with densely branched structures having a large number of end groups. A dendritic polymer includes several layers or generations of repeating units which all contain one or more branch points. Dendritic polymers, including dendrimers and hyperbranched polymers, are prepared by condensation reactions of monomeric units having at least two different types of reactive groups. Dendrimers are highly symmetric, whereas macromolecules designated as hyperbranched may to a certain degree hold an asymmetry, yet maintaining the highly branched treelike structure.

Dendritic macromolecules normally consist of an initiator or nucleus having one or more reactive sites and a number of branching layers and optionally a layer of chain terminating molecules. Continued replication of branching layers normally yields increased branch multiplicity and, where applicable or desired, increased number of terminal groups. The layers are usually called generations and the branches dendrons.

These materials have found such diverse uses as catalysts (and catalyst supports), as selective membranes and coatings, as demulsifiers for oil-in-water emulsions, as wet strength agents in the manufacture of paper, as agents for modifying viscosities in aqueous formulations such as paints, as impact modifiers or as cross-linking agents in plastics, as carriers for agricultural, pharmaceutical and other substances, and as submicron size calibrators.

Certain dendritic polymers have been suggested for use in the context of personal care.

WO97/14404 describes personal wash compositions containing an anionic surfactant as a cleaning agent and a cationic dendrimer as a mildness aid. The preferred cationic dendrimers are polyamidoamine (PAMAM) dendrimers prepared by sequential reactions of ethylenediamine and methyl acrylate.

U.S. Pat. No. 5,449,519 relates to keratolytic or anti-acne compositions in which the keratolytic or anti-acne agent (e.g. salicylic acid) is complexed with a starburst dendrimer of the PAMAM type.

EP 0 880 961 and EP 880 962 describe anti-solar preparations for protection of skin and hair containing a hyperbranched or dendrimeric polyamino-polymer such as hyperbranched polyethyleneimine.

EP 0 858 797 describes deodorant compositions comprising dendrimers having primary amine terminal groupings.

EPO 884 047 relates to the use of polyamine polymers, which may be hyperbranched or dendrimeric, as antioxidant agents for cosmetic or dermatological compositions.

WO 99/32076 and WO 99/32540 concern the use of certain specific disulphide-functionalised hyperbranched polymers and dendrimers in cosmetics and pharmaceuticals as thickening or gelling agents or as film-forming agents.

EP 0 815 827 describes cosmetic compositions for treating the hair with a content of at least one dendrimer or dendrimer conjugate in a cosmetic base. The compositions preferably contain dendrimers that are prepared from a 1,4-diaminobutane nucleus via the stepwise Michael addition of acrylonitrile followed by catalytic hydrogenation of cyano groups to amino groups. These dendrimers are referred to as poly(iminopropane-1,3-diyl) dendrimers with nitrile or amino terminal groups and their preparation is describes in U.S. Pat. No. 5,530,092. The compositions are said to provide an appreciable reduction in combing force, based on tests in aqueous solution comparing examples of the above described nitrile/amino functionalised dendrimers with standard hair care polymers such as vinylpyrrolidone/dimethylaminoethylmethacrylate copolymer.

None of the above documents disclose or suggest the utility of dendritic polyols in cosmetic and personal care compositions such as hair styling compositions.

SUMMARY OF THE INVENTION

The present invention provides a cosmetic and personal care composition comprising a hydroxyl-functionalised dendritic macromolecule.

DETAILED DESCRIPTION

Hydroxyl-functionalised Dendritic Macromolecule

The composition of the present invention preferably contains a hydroxyl-functionalised dendritic macromolecule that is built up from polyester units.

Suitable materials are described in SE 468 771, which discloses a macromolecule which is composed of an initiator, having at least one hydroxyl group, to which initiator is added at least one branching generation comprising at least one chain extender, having at least one carboxyl group and at least two hydroxyl groups.

Further suitable materials are described in SE 503 342, in which the macromolecule is substantially composed of a nucleus, having at least one epoxide group, to which nucleus is added at least one branching generation comprising at least one chain extender, having at least three reactive functions of which at least one is a carboxyl or epoxide group and at least one is a hydroxyl group.

The above described materials are also referred to as polyhydric polyester alcohols or hyperbranched polyols. Preferably these materials have at least eight, more preferably at least sixteen, most preferably at least thirty-two terminal hydroxyl groupings per macromolecule. Their molecular weight is preferably at least 800, more preferably at least 1600, most preferably at least 2500 g/mole.

The above materials are available commercially from Perstorp AB, SE-284 80 Perstorp, Sweden under the trademark of BOLTORN. Examples of such materials are BOLTORN H10, BOLTORN H20, BOLTORN H30 and BOLTORN H40, of which BOLTORN H30 and BOLTORN H40 are preferred.

Cosmetic and Personal Care Compositions

Compositions of the present invention are preferably formulated into hair care compositions, especially hairspray compositions, but can also be formulated into a wide variety of product types, including mousses, gels, lotions, tonics, sprays, shampoos, conditioners, rinses, hand and body lotions, facial moisturisers, sunscreens, anti-acne preparations, topical analgesics, mascaras, and the like. The carriers and additional components required to formulate such products vary with product type and can be routinely chosen by one skilled in the art. The following is a description of some of these carriers and additional components.

Carriers

Hair care compositions of the present invention can comprise a carrier, or a mixture of such carriers, which are suitable for application to the hair. The carriers are present at from about 0.5% to about 99.5%, preferably from about 5.0% to about 99.5%, more preferably from about 10.0% to about 98.0%, of the composition. As used herein, the phrase "suitable for application to hair" means that the carrier does not damage or negatively affect the aesthetics of hair or cause irritation to the underlying skin.

Carriers suitable for use with hair care compositions of the present invention include, for example, those used in the formulation of hair sprays, mousses, tonics, gels, shampoos, conditioners, and rinses. The choice of appropriate carrier will also depend on the particular hydroxyl-functionalised dendritic macromolecule to be used, and whether the product formulated is meant to be left on the surface to which it is applied (e.g., hair spray, mousse, tonic, or gel) or rinsed off after use (e.g., shampoo, conditioner, rinse).

The carriers used herein can include a wide range of components conventionally used in hair care compositions. The carriers can contain a solvent to dissolve or disperse the particular hydroxyl-functionalised dendritic macromolecule being used, with water, the C1–C6 alcohols, lower alkyl acetate and mixtures thereof being preferred. The carriers can also contain a wide variety of additional materials such as acetone, hydrocarbons (such as isobutane, hexane, decene), halogenated hydrocarbons (such as Freons) and volatile silicones such as cyclomethicone.

When the hair care composition is a hair spray, tonic, gel, or mousse the preferred solvents include water, ethanol, volatile silicone derivatives, and mixtures thereof. The solvents used in such mixtures may be miscible or immiscible with each other. Mousses and aerosol hair sprays can also utilise any of the conventional propellants to deliver the material as a foam (in the case of a mousse) or as a fine, uniform spray (in the case of an aerosol hair spray). Examples of suitable propellants include materials such as trichlorofluoromethane, dichlorodifluoromethane, difluoroethane, dimethylether, propane, n-butane or isobutane. A tonic or hair spray product having a low viscosity may also utilise an emulsifying agent. Examples of suitable emulsifying agents include nonionic, cationic, anionic surfactants, or mixtures thereof. If such an emulsifying agent is used, it is preferably present at a level of from about 0.01% to about 7.5% by weight based on total weight of the composition. The level of propellant can be adjusted as desired but is generally from about 3% to about 30% by weight based on total weight for mousse compositions and from about 15% to about 50% by weight based on total weight for aerosol hair spray compositions. Suitable spray containers are well known in the art and include conventional, non-aerosol pump sprays i.e., "atomisers", aerosol containers or cans having propellant, as described above, and also pump aerosol containers utilising compressed air as the propellant.

Where the hair care compositions are conditioners and rinses the carrier can include a wide variety of conditioning materials. Where the hair care compositions are shampoos, the carrier can include, for example, surfactants, suspending agents, and thickeners.

The carrier can be in a wide variety of forms. For example, emulsion carriers, including oil-in-water, water-in-oil, water-in-oil-in-water, and oil-in-water-in-silicone emulsions, are useful herein. These emulsions can cover a broad range of viscosities, e.g., from about 100 cps to about 200,000 cps. These emulsions can also be delivered in the form of sprays using either mechanical pump containers or pressurised aerosol containers using conventional propellants. These carriers can also be delivered in the form of a mousse. Other suitable topical carriers include anhydrous liquid solvents such as oils, alcohols, and silicones (e.g., mineral oil, ethanol, isopropanol, dimethicone, cyclomethicone, and the like); aqueous-based single phase liquid solvents (e.g., hydro-alcoholic solvent systems); and thickened versions of these anhydrous and aqueous-based single phase solvents (e.g., where the viscosity of the solvent has been increased to form a solid or semi-solid by the addition of appropriate gums, resins, waxes, polymers, salts, and the like).

Additional Components

A wide variety of additional components can be employed in cosmetic and personal care compositions according to the present invention. Examples include the following:

hair styling polymers for hair styling compositions such as hair sprays, gels, and mousses. Hair styling polymers are well known articles of commerce and many such polymers are available commercially which contain moieties which render the polymers cationic, anionic, amphoteric or nonionic in nature. The polymers may be synthetic or naturally derived.

The amount of the polymer may range from 0.5 to 10%, preferably 0.75 to 6% by weight based on total weight of the composition.

Examples of anionic hair styling polymers are:

copolymers of vinyl acetate and crotonic acid;

terpolymers of vinyl acetate, crotonic acid and a vinyl ester of an alpha-branched saturated aliphatic monocarboxylic acid such as vinyl neodecanoate;

copolymers of methyl vinyl ether and maleic anhydride (molar ratio about 1:1) wherein such copolymers are 50% esterified with a saturated alcohol containing from 1 to 4 carbon atoms such as ethanol or butanol;

acrylic copolymers containing acrylic acid or methacrylic acid as the anionic radical-containing moiety with other monomers such as: esters of acrylic or methacrylic acid with one or more saturated alcohols having from 1 to 22 carbon atoms (such as methyl methacrylate, ethyl acrylate, ethyl methacrylate, n-butyl acrylate, t-butyl acrylate, t-butyl methacrylate, n-butyl methacrylate, n-hexyl acrylate, n-octyl acrylate, lauryl methacrylate and behenyl acrylate); glycols having from 1 to 6 carbon atoms (such as hydroxypropyl methacrylate and hydroxyethyl acrylate); styrene; vinyl caprolactam; vinyl acetate; acrylamide; alkyl acrylamides and methacrylamides having 1 to 8 carbon atoms in the alkyl group (such as methacrylamide, t-butyl acrylamide and n-octyl acrylamide); and other compatible unsaturated monomers.

The polymer may also contain grafted silicone, such as polydimethylsiloxane.

Specific examples of suitable anionic hair styling polymers are:

RESYN® 28-2930 available from National Starch (vinyl acetate/crotonic acid/vinyl neodecanoate copolymer);

ULTRAHOLD® 8 available from BASF (CTFA designation Acrylates/acrylamide copolymer);

the GANTREZ®ES series available from ISP corporation esterified copolymers of methyl vinyl ether and maleic anhydride).

Other suitable anionic hair styling polymers include carboxylated polyurethanes. Carboxylated polyurethane resins are linear, hydroxyl-terminated copolymers having pendant carboxyl groups. They may be ethoxylated and/or propoxylated at least at one terminal end. The carboxyl group can be a carboxylic acid group or an ester group, wherein the alkyl moiety of the ester group contains one to three carbon atoms. The carboxylated polyurethane resin can also be a copolymer of polyvinylpyrrolidone and a polyurethane, having a CTFA designation PVP/polycarbamyl polyglycol ester. Suitable carboxylated polyurethane resins are disclosed in EP 0 619 111 A1 and U.S. Pat. No. 5,000,955. Other suitable hydrophilic polyurethanes are disclosed in U.S. Pat. Nos. 3,822,238; 4,156,066; 4,156,067; 4,255,550; and 4,743,673.

Amphoteric hair styling polymers which can contain cationic groups derived from monomers such as t-butyl aminoethyl methacrylate as well as carboxyl groups derived from monomers such as acrylic acid or methacrylic acid can also be used in the present invention. One specific example of an amphoteric hair styling polymer is Amphomer® (Octylacrylamide/acrylates/butylaminoethyl methacrylate copolymer) sold by the National Starch and Chemical Corporation.

Examples of nonionic hair styling polymers are homopolymers of N-vinylpyrrolidone and copolymers of N-vinylpyrrolidone with compatible nonionic monomers such as vinyl acetate.

Nonionic polymers containing N-vinylpyrrolidone in various weight average molecular weights are available commercially from ISP Corporation—specific examples of such materials are homopolymers of N-vinylpyrrolidone having an average molecular weight of about 630,000 sold under the name PVP K-90 and are homopolymers of N-vinylpyrrolidone having an average molecular weight of about 1,000,000 sold under the name of PVP K-120.

Other suitable nonionic hair styling polymers are crosslinked silicone resins or gums. Specific examples include rigid silicone polymers such as those described in EP-A-240 350 and cross-linked silicone gums such as those described in WO 96/31188.

Examples of cationic hair styling polymers are copolymers of amino-functional acrylate monomers such as lower alkyl aminoalkyl acrylate, or methacrylate monomers such as dimethylaminoethyl methacrylate, with compatible monomers such as N-vinylpyrrolidone, vinyl caprolactam, alkyl methacrylates (such as methyl methacrylate and ethyl methacrylate) and alkyl acrylates (such as ethyl acrylate and n-butyl acrylate).

Specific examples of suitable cationic polymers are:

copolymers of N-vinylpyrrolidone and dimethylaminoethyl methacrylate, available from ISP Corporation as Copolymer 845, Copolymer 937 and Copolymer 958;

copolymers of N-vinylpyrrolidone and dimethylaminopropylacrylamide or methacrylamide, available from ISP Corporation as Styleze® CC10;

copolymers of N-vinylpyrrolidine and dimethylaminoethyl methacrylate;

copolymers of vinylcaprolactam, N-vinylpyrrolidone and dimethylaminoethylmethacrylate;

Polyquaternium-4 (a copolymer of diallyldimonium chloride and hydroxyethylcellulose);

Polyquaternium-11 (formed by the reaction of diethyl sulphate and a copolymer of vinyl pyrrolidone and dimethyl aminoethylmethacrylate), available from ISP as Gafquate® 734, 755 and 755N, and from BASF as Luviquat® PQ11;

Polyquaternium-16 (formed from methylvinylimidazolium chloride and vinylpyrrolidone), available from BASF as Luviquat® FC 370, FC 550, FC 905 and HM-552;

Polyquaternium-46 (prepared by the reaction of vinylcaprolactam and vinylpyrrolidone with methylvinylimidazolium methosulphate), available from BASF as Luviquat®Hold.

Examples of suitable naturally-derived polymers include shellac, alginates, gelatins, pectins, cellulose derivatives and chitosan or salts and derivatives thereof. Commercially available examples include Kytamer® (ex Amerchol) and Amaze® (ex National Starch).

With certain of the above-described polymers it may be necessary to neutralise some acidic groups to promote solubility/dispersibility. Examples of suitable neutralising agents include 2-amino-2- methyl-1,3-propanediol (AMPD); 2-amino-2-ethyl-1,3-propanediol (AEPD); 2-amino-2-methyl-1-propanol (AMP); 2-amino-1-butanol (AB); monoethanolamine (MEA); diethanolamine (DEA); triethanolamine (TEA); monoisopropanolamine (MIPA); diisopropanol-amine (DIPA); triisopropanolamine (TIPA); and dimethyl stearamine (DMS). A long chain amine neutralising agent such as stearamidopropyl dimethylamine or lauramidopropyl dimethylamine may be employed, as is described in U.S. Pat. No. 4,874,604. Also suitable are inorganic neutralisers, examples of which include sodium hydroxide, potassium hydroxide and borax. Mixtures of any of the above neutralising agents may be used. Amounts of the neutralising agents will range from about 0.001 to about 10% by weight of the total composition.

sunscreening agents such as 2-ethylhexyl p-methoxycinnamate, 2-ethylhexyl N,N-dimethyl-p-aminobenzoate, p-aminobenzoic acid, 2-phenylbenzimidazole-5-sulfonic acid, octocrylene, oxybenzone, homomenthyl salicylate, octyl salicylate, 4,4'-methoxy-t-butyldibenzoylmethane, 4-isopropyl dibenzoylmethane, 3-benzylidene camphor, 3-(4-methylbenzylidene) camphor, titanium dioxide, zinc oxide, silica, iron oxide, and mixtures thereof.

anti-dandruff actives such as zinc pyrithione, piroctone olamine, selenium disulphide, sulphur, coal tar, and the like.

hair conditioning agents such as hydrocarbons, silicone fluids, and cationic materials. The hydrocarbons can be either straight or branched chain and can contain from about 10 to about 16, preferably from about 12 to about 16 carbon atoms. Examples of suitable hydrocarbons are decane, dodecane, tetradecane, tridecane, and mixtures thereof.

Examples of suitable silicone conditioning agents useful herein can include either cyclic or linear polydimethylsiloxanes, phenyl and alkyl phenyl silicones, and silicone copolyols. Cationic conditioning agents useful herein can include quaternary ammonium salts or the salts of fatty amines.

surfactants for hair shampoo and conditioner compositions. For a shampoo, the level is preferably from about 10% to about 30%, preferably from 12% to about 25%, by weight based on total weight of the composition. For conditioners, the preferred level of surfactant is from about 0.2% to about 3%, by weight based on total weight of the composition. Surfactants useful in compositions of the present invention include anionic, nonionic, cationic, zwitterionic and amphoteric surfactants.

carboxylic acid polymer thickeners for hair shampoo and conditioner compositions. These crosslinked polymers contain one or more monomers derived from acrylic acid, substituted acrylic acids, and salts and esters of these acrylic acids and the substituted acrylic acids, wherein the crosslinking agent contains two or more carbon-carbon double bonds and derived from a polyhydric alcohol. Examples of carboxylic acid polymer thickeners useful herein are those selected from the group consisting of carbomers, acrylates/C10–C30 alkyl acrylate crosspolymers, and mixtures thereof. Compositions of the present invention can comprise from about 0.025% to about 1%, more preferably from about 0.05% to about 0.75% and most preferably from about 0.10% to about 0.50% of the carboxylic acid polymer thickeners, by weight based on total weight of the composition.

emulsifiers for emulsifying the various carrier components of the compositions of the invention. Suitable emulsifier types include polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate,Polysorbate 60, glyceryl stearate, PEG-100 stearate, and mixtures thereof. The emulsifiers can be used individually or as a mixture of two or more and can comprise from about 0.1% to about 10%, more preferably from about 1% to about 7%, and most preferably from about 1% to about 5%, by weight based on total weight of the composition.

vitamins and derivatives thereof (e.g., ascorbic acid, vitamin E, tocopheryl acetate, retinoic acid, retinol, retinoids, and the like.

cationic polymers (e.g., cationic guar gum derivatives such as guar hydroxypropyltrimonium chloride and hydroxypropyl guar hydroxypropyltrimonium chloride, available as the Jaguar® series from Rhone-Poulenc).

preservatives, antioxidants, chelators and sequestrants; and aesthetic components such as fragrances, colourings, hair nutrients and essential oils.

The invention will now be illustrated by the following non-limiting Examples:

EXAMPLES

Examples 1 to 3

The following hairspray formulations were made up, having ingredients shown in the Table below:

|  | % WEIGHT | | |
|---|---|---|---|
|  | Ex. 1 | Ex. 2 | Ex. 3 |
| Polyol[1] | 0.02 | 0.2 | 1.0 |
| AMPHOMER ®[2] | 1.98 | 1.8 | 1.0 |
| 2-Amino-2-methyl-1-propanol | 0.297 | 0.27 | 0.15 |
| SILWET ® L-7602[3] | 0.10 | 0.10 | 0.10 |
| DC200/10 cst[4] | 0.10 | 0.10 | 0.10 |
| Perfume | 0.15 | 0.15 | 0.15 |
| WATER | 2.0 | 2.0 | 2.0 |
| ETHANOL | 60.353 | 60.38 | 60.15 |
| CAP 40[5] | 35.0 | 35.0 | 35.0 |

The formulations of Examples 1 to 3 were tested against a control formulation in which the polyol[1] was omitted. In the tests, each of the formulations were sprayed individually onto hair samples. 12 panellists were then asked to make a comparative assessment of the hair samples so treated across a range of attributes.

Overall, the formulations of Examples 1 to 3 were clearly preferred to the control on the positive attributes of strength of hold imparted to the hair and softness of feel imparted to the hair.

The formulations of Examples 1 to 3 also gave perceivably less stickiness and deposits on the hair (both of which are undesirable attributes for a hairspray), compared with the control.

Example 4

The polyol[1] was evaluated by itself in ethanol solution for the properties of film formation, wash off and bond strength. The results were as follows:

Film Formation

Films cast from 10% w/v ethanol solutions of polyol[1] produced clear non-tacky films.

Wash Off

A hair switch (10.25 g of 2 inch Spanish hair) was coated with a 5% w/v ethanol solution of polyol[1] and air dried for 3 hours. The switch was washed with water only and air dried overnight. No residues were visible and no material coating could be felt. FT-IR AR analysis confirmed no polyol[1] present on hair surface.

Bond Strength

Diastron MTT600 analysis of crossed hair fibres in which 1 microliter of 5% w/v ethanol solution of polyol[1] had been pipetted onto the fibre-fibre junction showed that the polyol[1] was capable of bonding to hair with an average bond strength of 18.38 g.

For the purposes of comparison, a PAMAM Starburst dendrimer generation 1 (ex Aldrich) was subjected to an equivalent evaluation for the properties of film formation, wash off and bond strength. In contrast, this material did not form films or bond to hair and showed inferior wash off properties.

What is claimed is:

1. A cosmetic and personal care composition selected from the group consisting of hairspray compositions, mousses, gels, lotions, tonics, shampoos, and conditioners wherein said composition comprises a hydroxyl-functionalised dendritic macromolecule.

2. A composition according to claim 1, in which the hydroxyl-functionalised dendritic macromolecule is built up from polyester units.

3. A composition according to claim 1, which is formulated as a hairspray, gel or mousse.

4. A composition according to claim 3, further comprising an anionic, nonionic, cationic or amphoteric hair styling polymer.

5. A composition according to claim 3, further comprising an aerosol propellant.

6. A composition according to claim 1, wherein said hydroxyl-functionalised dendritic macromolecule is a polyhydric polyester alcohol or a hyperbranched polyol having at least 8 terminal hydroxyl groupings per macromolecule, and having a molecular weight of at least 800.

7. A cosmetic and personal care composition which is a hair styling composition which comprises a hydroxyl-functionalised dendritic macromolecule.

8. A composition in accordance with claim 7, which comprises:

(a) about 0.5 to about 10% of a hair styling polymer;

(b) about 0.02 to about 1.0% of hydroxyl-functionalised dendritic macromolecule;

(c) a silicone fluid; and (d) about 0.5 to about 99.5% of a carrier suitable for application to hair.

9. A composition in accordance with claim 1, which is a hair shampoo or a hair conditioner and which comprises:

(a) about 10% to about 30% of a surfactant;

(b) about 0.025 to about 1% of a carboxylic acid polymer thickener;

(c) about 0.1% to about 10% of an emulsifier;

(d) a cationic polymer;

(e) about 0.02 to about 1.0% of a hydroxyl-functionalised dendritic macromolecule; and (f) about 0.5 to about 99.5% of a carrier suitable for application to hair.

* * * * *